United States Patent
Kato et al.

(10) Patent No.: US 8,097,285 B2
(45) Date of Patent: Jan. 17, 2012

(54) USE OF SERICIN FOR IMPROVING THE FEELING IN USE OF DENTURE

(75) Inventors: Yoichi Kato, Fukui (JP); Kazuhisa Tsujimoto, Fukui (JP); Hideyuki Yamada, Fukui (JP); Taizo Hamada, Hiroshima (JP); Sadayuki Yuda, Osaka (JP); Koichi Okano, Shiga (JP)

(73) Assignee: Seiren Co., Ltd., Fukui (JP)

( * ) Notice: Subject to any disclaimer, the term of this patent is extended or adjusted under 35 U.S.C. 154(b) by 0 days.

(21) Appl. No.: 12/861,265

(22) Filed: Aug. 23, 2010

(65) Prior Publication Data

US 2011/0033824 A1   Feb. 10, 2011

Related U.S. Application Data

(62) Division of application No. 11/887,027, filed as application No. PCT/JP2006/306764 on Mar. 24, 2006, now abandoned.

(30) Foreign Application Priority Data

Mar. 25, 2005   (JP) .................................. 2005-89303
Mar. 25, 2005   (JP) .................................. 2005-89304

(51) Int. Cl.
*A61K 35/64*   (2006.01)

(52) U.S. Cl. .......................... 424/538; 424/401; 424/736
(58) Field of Classification Search .................... None
See application file for complete search history.

(56) References Cited

U.S. PATENT DOCUMENTS

| | | | |
|---|---|---|---|
| 3,691,272 | A | 9/1972 | Asche |
| 5,629,003 | A | 5/1997 | Horstmann et al. |
| 6,395,279 | B1 | 5/2002 | Empie et al. |
| 6,485,711 | B1 | 11/2002 | Olmstead |
| 6,821,963 | B2 | 11/2004 | Barrett et al. |
| 2001/0053759 | A1 | 12/2001 | Jin et al. |
| 2005/0064025 | A1 | 3/2005 | Litchenberger et al. |
| 2005/0079236 | A1 | 4/2005 | Ahrens |

FOREIGN PATENT DOCUMENTS

| | | |
|---|---|---|
| JP | 2004081837 | 3/2004 |
| WO | 0005049 | 2/2000 |
| WO | 2005000251 | 1/2005 |

OTHER PUBLICATIONS

Bio Ind. 2004, vol. 21, No. 3, pp. 46-53.

*Primary Examiner* — Susan Hoffman
(74) *Attorney, Agent, or Firm* — Dilworth & Barrese, LLP

(57) ABSTRACT

The purpose is to prevent, ameliorate or relieve various conditions induced in the dried oral cavity or to improve the stability of a denture during use. A solution for treating a denture or a denture stabilizer comprising sericin can be used.

16 Claims, No Drawings

USE OF SERICIN FOR IMPROVING THE FEELING IN USE OF DENTURE

The present application is a divisional application of U.S. application Ser. No. 11/887,027 filed Sep. 24, 2007 now abandoned and which is a U.S. national phase application of PCT application no. PCT/JP2006/306764 filed Mar. 24, 2006.

TECHNICAL FIELD

The present invention relates to a technique for improving the feeling in use of a denture. More particularly, the present invention is concerned with a denture surface treating agent capable of enhancing the biocompatibility of the denture surface and capable of preventing or ameliorating or relieve various symptoms such as dry feeling, unpleasant feeling, pain, dental caries, periodontal disease, tongue plaque and bad breath within an oral cavity during use of a denture, as well as a denture stabilizer to be used during use of a denture within an oral cavity, capable of enhancing the sense of stability of the denture during use and capable of preventing or ameliorating or relieving various symptoms induced by drying of the interior of the oral cavity such as intraoral cavity unpleasant feeling, pain, dental caries, periodontal disease, tongue plaque and bad breath.

BACKGROUND ART

Usually the interior of an oral cavity is constantly supplied with saliva. The saliva contains such a protein as albumin and such an inorganic component as salt and fulfills many functions which are important for maintaining an optimum oral cavity environment such as keeping wet the interior of the oral cavity, pH buffering action, antibacterial effect and intraoral cavity washing effect.

However, it is said that the amount of secreted saliva decreases as one gets old, and in the case of an aged person, the drying within the oral cavity caused by a decrease in the amount of secreted saliva poses a problem. Further, irrespective of age, there sometimes is a case where the amount of secreted saliva decreases markedly by the influence of various diseases and medicines used for treatment of the diseases or by stress or the like against complicated social life conditions, with consequent drying of the interior of the oral cavity.

Particularly, the drying within the oral cavity during use of a denture is a recent problem. There are many denture users who feel a heavy stress against a life with a denture inserted into the oral cavity, in various scenes of daily life. It is known that the secretion of saliva decreases to an extreme degree by such a stress.

When using a denture, there sometimes is a case where a paste- or sheet-like denture base stabilizing adhesive is used to bond and fix the denture and the intraoral cavity tissue strongly with each other lest the denture should come off. However, bonding the denture, which is a foreign matter to a living body, forcibly into the oral cavity gives a heavy stress to the user of the denture in both body and mind. Consequently, there arises the problem that, simultaneously with the start of use of the denture, the secretion of saliva decreases markedly or is exhausted and the interior of the oral cavity becomes dry.

Such an oral cavity drying disease is generally called dry mouth and is known to give rise to intraoral cavity burning sensation, pain, glossodynia, dental caries, taste trouble, inflammation of the oral mucosa, erosion, formation of ulcer, formation of tongue plaque, bad breath, periodontal disease, difficulty of chewing, dysphagia (swallowing trouble), and difficulty of conversation. Moreover, there sometimes occurs a case where the denture is not fixed due to drying in the interior of the oral cavity and is rubbed against the periodontal tissue, thus inducing pain to the extent that it is impossible to eat a meal or make conversation. This is an extremely serious problem. In the case where the interior of the oral cavity is thus dried, even if the mouth is washed out, the dried condition in the oral cavity is not ameliorated although the interior of the oral cavity gets wet temporarily, thus giving rise to a very large number of serious pains in daily life. Such being the case, a keen demand exists for an appropriate measure against such intraoral cavity drying.

In view of such circumstances, such a composition as moderately stimulates the salivary gland to wet the interior of the oral cavity is now under development in order to prevent, ameliorate or relieve the intraoral cavity drying. In JP Hei 10 (1998)-182392A it is proposed to use a sialogogic agent such as an organic acid. However, since acidity is very stimulative and the taste differs depending on each individual person; besides, the durability of effect is deficient. For these reasons the use of such a sialogogic agent is limited. For example, in the case where the saliva secreting function is markedly deteriorated due to an operation for treatment of a disease or by radiotherapy, the above method of stimulating the salivary gland does not afford a satisfactory saliva secretion promoting effect and the drying in the oral cavity is not remedied.

Further, the development of artificial saliva and that of a gargling agent are under way for the purpose of remedying the drying in the oral cavity. Heretofore proposed are artificial saliva and a gargling agent with glycerin or hyaluronic acid incorporated therein (JP 2004-136102A and WO 00-056344). However, since those components are not originally present in large amounts with the saliva, there sometimes is a case where the feeling of use is not desirable for the user or there is not obtained a satisfactory effect. In JP Hei 9 (1997)-508898A there is developed artificial saliva containing a salivary protein such as mucin or albumin. However, there sometimes is used a protein derived from a mammal such as pig, thus giving rise to the problem of safety against humans. Such artificial saliva and gargling agent have so far encountered problems in point of durability of effect, taste and feeling of use.

On the other hand, in WO 00-05049 there is proposed a method wherein a material having biocompatibility is contained in the interior of a denture to enhance the hydrophilicity of a biocontact surface of the denture, thereby making the denture more compatible with the interior of the oral cavity. According to this method, however, a heavy burden may be imposed on the user because it is necessary to remake the denture. Therefore, there has been a demand for a simpler method wherein the surface of an existing denture is modified so as to become more compatible with the interior of the oral cavity.

Such being the case, there still exists a demand for a remedial measure for preventing, ameliorating or relieving such a problem as intraoral cavity drying during use of a denture and improving the stability of the denture during use.

DISCLOSURE OF THE INVENTION

Object of the Invention

The object of the present invention is to remedy the above-mentioned problems. Particularly, the object of the invention is to provide a technique for improving the feeling in use of a denture which technique can enhance the compatibility of a cell contact surface of the denture with the intraoral cavity tissue, thereby wetting a dried interior of the oral cavity and giving a smooth feeling to the interior of the oral cavity to prevent, ameliorate or relieve various symptoms and states caused by intraoral cavity drying and improve the stability of the denture during use.

SUMMARY OF THE INVENTION

The present invention uses sericin for improving the above-mentioned various factors associated with the feeling in use of a denture.

A first mode of use of sericin in the present invention is the use of sericin as a treating agent for treating the surface of a denture.

A typical example of the denture surface treating agent in the above mode is the incorporation of sericin in a pretreating solution prior to loading of the denture into an oral cavity.

The denture surface treating agent according to the present invention is preferably a liquid treating agent with sericin present in the state of an aqueous solution.

A second mode of use of sericin in the present invention is the use of sericin as a stabilizer component for a denture.

The denture stabilizer in this mode contains sericin within a soft solid matter which is for fixing the denture to a predetermined position within an oral cavity.

In the denture stabilizer according to the present invention it is preferable that the soft solid matter containing sericin be disposed in at least a skin-contact portion of the stabilizer which lies between the loaded denture and the skin (including gums).

EMBODIMENTS OF THE INVENTION

The sericin used in the present invention is a silk protein and its average molecular weight is not specially limited, but is preferably 6,000 to 100,000, more preferably 8,000 to 40,000. If an average molecular weight of sericin is larger than 100,000, an aqueous solution thereof may occur gelation at a concentration of 0.5 wt % or so and thus there sometimes is a case where the mode of its use is limited. If an average molecular weight of sericin is smaller than 6,000, a satisfactory effect may not be obtained.

The source of sericin used in the present invention is not specially limited. As an extraction source there may be used, for example, silk gland of a domesticated silkworm or a wild silkworm, produced cocoon, raw silk, or silk fabric. For the extraction of sericin there may be adopted a known extraction method. For example, there may be adopted a method wherein cocoon, raw silk or silk fabric is treated with hot water or aqueous solution of acid, alkali or enzyme, by which sericin is partially hydrolyzed and extracted therefrom. Preferably, the sericin thus obtained is purified by a known method such as, for example, filtration, dialysis or ultrafiltration and dried, and the resulting powdered sericin as a substantially single protein is utilized. One having a purity of 90% or more is particularly preferred.

The surface treating agent in the first mode of use is preferably a liquid agent for treating the denture prior to loading it to a predetermined position within the oral cavity. Usually, sericin powder is dissolved or suspended in water, buffer solution, physiological saline or alcohol and the resulting solution or suspension is used as a denture surface modifier.

Particularly, it is preferable to use water as a main medium, and by adding thereto a polyhydric alcohol and/or a plant extract it is possible to enhance the denture surface modifying effect. As polyhydric alcohols employable in the present invention there are mentioned, for example, glycerin, propylene glycol, polyethylene glycol, and sorbitol. As plant extracts employable in the present invention there are mentioned, for example, grapefruit extract, olive extract, tea extract, low striped bamboo extract, sesame extract, safflower extract, and gingko extract.

The concentration of sericin in the surface treating agent is preferably 0.01 to 10 wt %, more preferably 0.1 to 1 wt %. If the sericin concentration is lower than 0.01 wt %, the denture surface modifying effect will not be attained, and if it exceeds 10 wt %, there may occur an excessive stickiness during use of the denture and the user will have an unpleasant feeling. The concentration of the plant extract used is preferably 0.001 to 10 wt %, more preferably 0.01 to 0.1 wt %. If the plant extract concentration is lower than 0.001 wt %, there will not be attained a satisfactory denture surface modifying effect, nor will be attained a synergistic effect with sericin. If it exceeds 10 wt %, no difference in effect will be recognized and an increase of cost will result. The concentration of the polyhydric alcohol used is preferably 0.1 to 50 wt %, more preferably 1 to 20 wt %. If it is lower than 0.1 wt %, a satisfactory denture surface modifying effect will not be attained, and a polyhydric alcohol concentration exceeding 50 wt % may result in the user having an unpleasant feeling within the oral cavity.

In the present invention, as known well, the denture is an artificial substitute for teeth and includes dentures from a removable partial denture up to a full denture. The type of the denture in the present invention is not specially limited, but a preferred type is a gingival denture comprising a base and an artificial tooth.

How to apply the denture surface treating agent in the present invention is not specially limited insofar as the surface treating agent is applied to a denture. Usually, the denture is immersed for example overnight within the foregoing sericin-containing solution or is washed by the said solution.

In this case, as a medium there may be used any of various commonly-used compositions for an oral cavity. The compositions for an oral cavity are products intended to prevent, ameliorate or relieve symptoms caused by drying within an oral cavity. It is used, for example, in tablet for gargling, mouth rinse solution, troche, intraoral patch, artificial saliva, spray for an oral cavity, denture stabilizer, buffer material for a denture, dentifrice, gel, ointment for an oral cavity (cream), granule, powder, jelly, gum, and candy.

As components of the denture surface treating agent in the present invention, known components conforming to the type of the surface treating agent may be used in their normally-used quantities other than the above components. For example, a binder, a thickener, an emulsifier and a dispersant may be used as necessary in combination with sericin (a polyhydric alcohol and/or a plant extract, if necessary). Further, where required, there may be used a pharmacologically active component, a preservative, a colorant, a sweetening material and a perfume may be used.

Since the denture surface treating agent according to the present invention exhibits its effect as a saliva protein and therefore an oral cavity composition containing the surface treating agent exhibits a buffer action between the denture and the intraoral cavity tissue, whereby it is possible to remedy or relieve the sense of incongruity, unpleasant feeling and intraoral cavity pain while the denture as a foreign matter to the human body is in contact with the intraoral cavity tissue. As a result, chewing and conversation of the denture user are more activated than before, thus leading to improvement of the saliva secreting function and amelioration of symptoms induced by intraoral cavity drying.

The denture surface treating agent according to the present invention is applicable not only to dentures for humans but also widely to dentures for mammals such as dogs.

The denture stabilizer in the second mode of use according to the present invention is usually constituted by a soft solid material containing sericin and lies between the denture and the intraoral cavity skin (e.g., gums). It is preferable that sericin be contained in the denture stabilizer in at least a portion which is in contact with the skin.

The soft solid material has such a softness as can be deformed with a denture loading force into the oral cavity. Usually, it is used in the form of a gel- or sheet-like material comprising a soft material such as any of various thickening natural polysaccharides and sericin incorporated therein.

As the soft material there may be used a suitable material heretofore employed for fixing and stabilizing a denture within an oral cavity. Typical examples thereof are thickening natural polysaccharides.

As examples of thickening natural polysaccharides employable preferably in the denture stabilizer according to the present invention, mention may be made of xanthan gum, tamarind, carrageenan, locust bean gum, guar gum, glucomannan, sorbitol, starch, dextrin, gelatin, carboxymethyl cellulose, hydroxyethyl cellulose, alginic acid, glycerin, and salts thereof.

The concentration of sericin in the soft solid material is preferably 0.01 to 40 wt %, more preferably 0.1 to 20 wt %. If the sericin concentration is lower than 0.01 wt %, a satisfactory effect may not be obtained, and if it exceeds 40 wt %, the user may have an unpleasant feeling during use of the denture. The concentration of the thickening natural polysaccharide used in the present invention is preferably 0.01 to 40 wt %, more preferably 0.1 to 20 wt %. If the polysaccharide concentration is lower than 0.01 wt %, a satisfactory effect may not be attained, and if it exceeds 40 wt %, the user may feel unpleasant.

Other known denture stabilizer components may be used in their normally-used quantities in combination with the denture stabilizer in the present invention. Examples of such components include non-toxic oils and fats and waxes, emulsifiers, dispersants, pharmacologically active components, preservatives, colorants, sweetening materials, perfumes, and inorganic salts.

As examples of non-toxic oils and fats and waxes there are mentioned vaseline, liquid paraffin, vegetable hardened oil, and beeswax. As examples of preservatives there are mentioned paraoxybenzoic acid, grapefruit extract, polylysine, and sodium benzoate. As examples of pharmacologically active components there are mentioned known anti-inflammatory drugs, analgesics, growth factors, antibacterial agents, and vitamin compounds. As examples of inorganic salts are mentioned sodium salts, potassium salts, calcium salts, and magnesium salts.

In the denture stabilizer according to the present invention, a composition comprising sericin and suitable components referred to above is applied to a fabric such as woven fabric, knitted fabric or nonwoven fabric comprising various fibers or to a film of a synthetic or natural material to afford a sheet-like form or formulation ingredients are formed into a sheet-like form, then the sheet-like product is disposed between the denture base and the intraoral cavity tissue, whereby the denture can be fixed. Further, in connection with the sericin-containing denture stabilizer according to the present invention, there may be adopted a method wherein suitable components referred to above are mixed into a gel form and the gel is then applied to the denture base portion which comes into contact with the intraoral cavity tissue, thereby making it possible to fix the denture and the intraoral cavity tissue to each other.

The following are formulation examples of denture stabilizing compositions which the present invention provides by combining the foregoing components.

Formulation Example 1

| | |
|---|---|
| Sericin | 1.00 g |
| Glucomannan | 1.50 g |
| Antiseptic | 0.15 g |
| Water | balance |
| Total | 100.00 g |

Formulation Example 2

| | |
|---|---|
| Sericin | 1.00 g |
| Sodium alginate | 4.00 g |
| Antiseptic | 0.15 g |
| Water | balance |
| Total | 100.00 g |

Formulation Example 3

| | |
|---|---|
| Sericin | 1.00 g |
| Xanthan gum | 4.00 g |
| Water | balance |
| Total | 100.00 g |

Formulation Example 4

| | |
|---|---|
| Sericin | 1.00 g |
| Antiseptic | 0.15 g |
| Vaseline | balance |
| Total | 100.00 g |

Formulation Example 5

| | |
|---|---|
| Sericin | 1.00 g |
| Sodium alginate | 5.00 g |
| Glycerin | 20.00 g |
| Antiseptic | 0.15 g |
| Water | balance |
| Total | 100.00 g |

Formulation Example 6

| | |
|---|---|
| Sericin | 1.00 g |
| Carrageenan | 4.00 g |
| Water | balance |
| Total | 100.00 g |

Formulation Example 7

| | |
|---|---|
| Sericin | 1.00 g |
| Tamarind | 4.00 g |
| Water | balance |
| Total | 100.00 g |

Formulation Example 8

| | |
|---|---|
| Sericin | 1.00 g |
| Guar gum | 1.50 g |
| Water | balance |
| Total | 100.00 g |

Formulation Example 9

| | |
|---|---|
| Sericin | 1.00 g |
| Locust bean gum | 3.00 g |
| Water | balance |
| Total | 100.00 g |

Formulation Example 10

| | |
|---|---|
| Sericin | 1.00 g |
| Glycerin | 20.00 g |
| Xanthan gum | 1.00 g |
| Antiseptic | 0.20 g |
| Potassium chloride | 120 mg |
| Sodium chloride | 85 mg |
| Dipotassium hydrogen phosphate | 35 mg |
| Calcium chloride dihydrate | 15 mg |
| Magnesium chloride hexahydrate | 5 mg |
| Water | balance |
| Total | 100.00 g |

Formulation Example 11

| | |
|---|---|
| Sericin | 1.00 g |
| Glucomannan | 1.50 g |
| Glycerin | 20.00 g |
| Antiseptic | 0.15 g |
| Potassium chloride | 120 mg |
| Sodium chloride | 85 mg |
| Dipotassium hydrogen phosphate | 35 mg |
| Calcium chloride dihydrate | 15 mg |
| Magnesium chloride hexahydrate | 5 mg |
| Water | balance |
| Total | 100.00 g |

Since the sericin contained in the denture stabilizer of the present invention has the effect as a saliva protein, the denture stabilizer of the present invention exhibits a buffer action between the denture and the intraoral cavity tissue, whereby it is possible to ameliorate or relieve a sense of incongruity, unpleasant feeling and pain in the oral cavity when the denture and the denture stabilizing composition, which are foreign matters to the human body, are in contact with the intraoral cavity tissue. Consequently, chewing and conversation of the denture user are more activated than before, which eventually leads to improvement of the saliva secreting function and amelioration of symptoms induced by intraoral cavity drying. Further, the denture stabilizing composition of the present invention is widely applicable not only to humans but also to mammals.

Effect of the Invention

The denture surface treating agent of the present invention can enhance the compatibility between the intraoral tissue contact surface of a denture and the intraoral cavity tissue, wet a dry interior of the oral cavity, give a smooth feeling to the interior of the oral cavity, and prevent, ameliorate or relieve various symptoms such as intraoral cavity unpleasant feeling, dental caries, periodontal disease, intraoral cavity pain, tongue plaque and bad breath which would be caused by drying the oral cavity. Moreover, the denture surface treating agent of the present invention has excellent biocompatibility, exhibits an excellent buffer action between a denture as an artificial tooth and the intraoral cavity tissue, and solves such problems as a sense of incongruity in an oral cavity, unpleasant feeling and pain in the oral cavity during use of the denture.

Further, since the denture surface treating agent of the present invention uses sericin which is utilized in food, cosmetics and suture threads for operations, it is highly safe and does not have any offensive taste, smell or color, so is best suited for use within an oral cavity.

The denture stabilizer of the present invention can enhance the stable feeling during use of a denture, wet the interior of a dry oral cavity, give a smooth feeling into an oral cavity, and further can prevent, ameliorate or relieve various symptoms and states induced by intraoral cavity drying such as unpleasant feeding within the oral cavity, dental caries, periodontal disease, intraoral cavity pain, tongue plaque and bad breath. Moreover, the denture stabilizer of the present invention has excellent biocompatibility and exhibits a buffer action between a denture as an artificial tooth and the intraoral cavity tissue, thereby solving such problems as a sense of incongruity in an oral cavity, unpleasant feeling and intraoral cavity pain.

Further, since the denture stabilizer of the present invention uses sericin which is utilized in food, cosmetics and suture threads for operations, it is highly safe and does not have any offensive taste, smell or color, so is best suited for its application to the interior of an oral cavity.

EXAMPLES

The present invention will be described below concretely by way of working Examples, but is not limited by the following Examples.

A. Denture Surface Treating Agent

Examples 1-3

In these Examples there was used sericin (powder) with a purity of 90% or more, obtained from cocoon or raw silk by extracting with an aqueous alkali solution thereby partially hydrolyzing sericin contained therein followed by purification and drying. An average molecular weight of the sericin was measured by gel filtration chromatography and was found to be about 20,000.

(Preparing a Denture Storage Solution)

Sericin, grapefruit extract and glycerin were added in the concentrations shown in Table 1 into pure water to prepare denture storage solutions having a function as a denture surface modifying agent.

TABLE 1

|  | Example 1 | Example 2 | Example 3 |
|---|---|---|---|
| Sericin | 1.0% (w/v) | 1.0% (w/v) | 1.0% (w/v) |
| Grapefruit Extract | — | 0.2% (w/v) | 0.2% (w/v) |
| Glycerin | — | — | 20.0% (w/v) |

(Evaluating Hydrophilicity of Denture Base Surface)

A chip of a denture base material was fabricated using PHYSIORESIN (a product of NISSIN CO., LTD) and a hydrophilizing effect of the denture base surface using the above denture storage solution was evaluated. The denture base was immersed in the denture storage solution for 30 minutes and was washed with running water for 0 second, 30 seconds, 1 minute, 5 minutes, 15 minutes and 30 minutes, then the water on the denture base surface was wiped off using filter paper. 2 µL of water was dropwise added to the denture base surface and a contact angle of a water droplet was measured to evaluate hydrophilicity. A goniometer type contact angle measuring device (a product of Eruma Kogaku K.K.) was used for measuring the contact angle. As a comparative example, the same test as above was conducted using pure water. The results are shown in Table 2.

TABLE 2

| | Washing Time | Comparative Example (Pure Water) | Example 1 | Example 2 | Example 3 |
|---|---|---|---|---|---|
| Contast Angle (degree) | 0 sec | 67.0 | 43.4 | 21.0 | 12.8 |
| | 30 sec | 67.2 | 47.4 | 43.2 | 42.6 |
| | 1 min | 67.5 | 48.5 | 46.6 | 44.2 |
| | 5 min | 68.2 | 51.2 | 50.6 | 47.5 |
| | 15 min | 68.3 | 53.1 | 53.8 | 47.8 |
| | 30 min | 68.7 | 54.7 | 53.5 | 48.3 |

From the results shown in the above Table 2 it is seen that the water droplet contact angle on the denture base surface becomes smaller with use of sericin. Also after the washing with pure water, a state higher in hydrophilicity than in the use of pure water was maintained. That is, with use of sericin, the denture base surface was modified and the wettability of the denture base surface, which is originally hydrophobic, was greatly improved. Moreover, it was turned out that by adding a grapefruit extract so as to be 0.2% in its concentration the denture base becomes more hydrophilic than in the use of sericin alone, thus affording a synergistic effect with sericin. Further, it is seen that by adding glycerin so as to be 20.0% in its concentration the wettability of the denture base is improved over a single use of sericin and over the combination of sericin and grapefruit extract and that there is obtained a synergistic effect with sericin and grapefruit extract.

(Monitor Test of Denture Surface Modifying Effect)

The denture surface modifying effect was evaluated using the denture storage solutions prepared above. A denture was immersed in each of the denture storage solutions and was then taken out, thereafter it was loaded into the intraoral cavity tissue and a sense of incongruity, pain, taste and intraoral cavity wetting during use of the denture were evaluated. As a comparative example, the same test as above was conducted using pure water.

The results of the monitor test are shown in Table 3. The symbols appearing in the table represent evaluation results as follows:

++ . . . satisfactory
+ . . . slightly satisfactory
− . . . unsatisfactory
± . . . neither satisfactory nor unsatisfactory

TABLE 3

| Evaluation Item | Panelist | Comparative Example (Pure Water) | Example 1 | Example 2 | Example 3 |
|---|---|---|---|---|---|
| Incongruity Sense Upon Loading | 1 | − | ± | + | + |
| | 2 | − | + | ++ | ++ |
| | 3 | − | ± | + | ++ |
| | 4 | − | ± | ++ | ++ |
| Slightness of Pain | 1 | − | ± | + | + |
| | 2 | − | + | ++ | ++ |
| | 3 | − | ± | + | ++ |
| | 4 | − | + | ++ | ++ |
| Taste | 1 | − | − | ± | ++ |
| | 2 | − | ± | ± | ++ |
| | 3 | − | ± | ± | ++ |
| | 4 | − | ± | ± | ++ |
| Intraoral Cavity Wetting | 1 | − | ± | ± | + |
| | 2 | − | + | + | ++ |
| | 3 | − | + | + | ++ |
| | 4 | − | ± | ++ | ++ |

From the results shown in Table 3 it is seen that unpleasant feeling upon loading of the denture can be ameliorated or relieved in all of Examples 1 to 3. Particularly, intraoral cavity pain induced by intraoral cavity drying was relieved and the secretion of saliva was improved.

B. Denture Stabilizer

Examples 4 and 5

In these Examples there was used sericin, obtained from cocoon or raw silk by extracting with an aqueous alkali solution thereby partially hydrolyzing sericin contained therein followed by purification and drying. An average molecular weight of the sericin was measured by gel filtration chromatography and was found to be about 20,000.

(Sheet-Like Denture Stabilizers Having Wetting Effect)

Compositions shown in Table 4 were each applied to non-woven cotton cloth (BENRYZE PS 170, a product of Asahi Chemical Industry Co., Ltd.) and dried to afford denture stabilizers having a wetting effect. Application quantities per cloth weight of composition ingredients are shown in Table 4 below.

TABLE 4

| Ingredient | Comparative Example 2 | Example 4 |
|---|---|---|
| Sericin | — | 20.000% (w/w) |
| Xanthan gum | 40.000% (w/w) | 40.000% (w/w) |
| Potassium chloride | 1.385% (w/w) | 1.385% (w/w) |
| Sodium chloride | 0.981% (w/w) | 0.981% (w/w) |
| Dipotassium hydrogen phosphate | 0.404% (w/w) | 0.404 (w/w) |
| Calcium chloride | 0.173% (w/w) | 0.173% (w/w) |
| Magnesium chloride | 0.058% (w/w) | 0.058% (w/w) |

(Monitor Evaluation Test of Sheet-Like Denture Stabilizers)

Monitor evaluation was performed using the denture stabilizers prepared in the above Comparative Example 2 and Example 4. Those denture stabilizers were immersed in pure water and then were each affixed to a denture base. In this state evaluation was made with respect to such items as denture stable feeling, compatibility with the intraoral cavity tissue, amelioration of pain, and amelioration of bad breath.

The results of the monitor evaluation test are shown in Table 5. The symbols appearing in the same table represent such evaluation results as +: satisfactory, −: unsatisfactory, and ±: neither satisfactory nor unsatisfactory.

As is seen from the results shown in Table 5, with ±respect to the denture stabilizer of Example 4 containing sericin, unpleasant feeling upon loading of the denture was ameliorated or relieved. Particularly, the ameliorating/relieving effect was high with respect to the sense of incongruity when loading the denture which is a foreign matter to the human body.

TABLE 5

| Evaluation Item | Panelist | Comparative Example 2 | Example 4 |
|---|---|---|---|
| Denture Stable Feeling | 1 | + | + |
| | 2 | ± | + |
| | 3 | ± | + |
| | 4 | + | + |
| Compatibility with Intraoral Cavity Tissue | 1 | ± | + |
| | 2 | − | + |
| | 3 | ± | + |
| | 4 | − | + |
| Amelioration of Pain | 1 | ± | + |
| | 2 | − | + |
| | 3 | ± | + |
| | 4 | ± | + |
| Amelioration of Bad Breath | 1 | ± | + |
| | 2 | + | + |
| | 3 | ± | + |
| | 4 | ± | + |

(Gel-Like Denture Stabilizers Having Wetting Effect)

Gel-like denture stabilizers having a wetting effect were prepared using the ingredients shown in Table 6. Amounts of the ingredients are shown in the same table.

TABLE 6

| Ingredient | Comparative Example 3 | Example 5 |
|---|---|---|
| Sericin | — | 1.000% (w/w) |
| Glucomannan | 1.500% (w/w) | 1.500% (w/w) |
| Glycerin | 20.000% (w/w) | 20.000% (w/w) |
| Potassium chloride | 0.120% (w/w) | 0.120% (w/w) |
| Sodium chloride | 0.085% (w/w) | 0.085% (w/w) |
| Dipotassium hydrogen phosphate | 0.035% (w/w) | 0.035% (w/w) |
| Calcium chloride dihydrate | 0.015% (w/w) | 0.015% (w/w) |
| Magnesium chloride hexahydrate | 0.005% (w/w) | 0.005% (w/w) |
| Grapefruit extract | 0.100% (w/w) | 0.100% (w/w) |

(Monitor Evaluation Test of Gel-Like Denture Stabilizers)

Monitor evaluation was conducted using the denture stabilizers prepared in the above Comparative Example 3 and Example 5. Those denture stabilizers were each affixed to a denture base and evaluation was made with respect to such items as denture stable feeling, compatibility with the intraoral cavity tissue, amelioration of pain, and amelioration of bad breath.

The results of the monitor evaluation test are shown in Table 7. The symbols appearing in the same table represent such evaluation results as +: satisfactory, −: unsatisfactory, and ±: neither satisfactory nor unsatisfactory.

As is seen from the results shown in Table 7, unpleasant feeling upon loading of the denture was ameliorated or relieved in Example 5 which contains sericin. Particularly, the compatibility with the intraoral cavity tissue was ameliorated and there was attained a high ameliorating/relieving effect with respect to the sense of incongruity when loading the denture which is a foreign matter to the human body.

TABLE 7

| Evaluation Item | Panelist | Comparative Example 3 | Example 5 |
|---|---|---|---|
| Denture Stable Feeling | 1 | ± | + |
| | 2 | ± | + |
| | 3 | − | + |
| | 4 | − | + |
| Compatibility with Intraoral Cavity Tissue | 1 | − | + |
| | 2 | − | + |
| | 3 | ± | + |
| | 4 | − | + |
| Amelioration of Pain | 1 | ± | + |
| | 2 | ± | + |
| | 3 | ± | + |
| | 4 | ± | + |
| Amelioration of Bad Breath | 1 | ± | + |
| | 2 | ± | + |
| | 3 | ± | + |
| | 4 | ± | + |

The invention claimed is:

1. Method for improving the feeling in use of a denture comprising the step of either treating a surface of the denture with a denture surface treating agent containing sericin prior to loading the denture into an oral cavity or disposing a denture stabilizer containing sericin between the denture and an intraoral cavity skin when the denture is loaded into the oral cavity.

2. The method as set forth in claim 1, wherein the denture surface treating agent is a liquid agent.

3. The method as set forth in claim 1, wherein the denture surface treating agent further contains plant extract.

4. The method as set forth in claim 1, wherein the denture surface treating agent further contains a polyhydric alcohol.

5. The method as set forth in claim 1, wherein the concentration of the sericin is 0.01% to 10% by weight in the denture surface treating agent.

6. The method as set forth in claim 3, wherein the concentration of the plant extract is 0.001% to 10% by weight in the denture surface treating agent.

7. The method as set forth in claim 4, wherein the concentration of the polyhydric alcohol is 0.1% to 50% by weight in the denture surface treating agent.

8. The method as set forth in claim 1, wherein the denture stabilizer is soft solid matter.

9. The method as set forth in claim 1, wherein the denture stabilizer further contains a thickening natural polysaccharide which is selected from at least one of xanthan gum, tamarind, carrageenan, locust bean gum, guar gum, glucomannan, sorbitol, starch, dextrin, gelatin, carboxymethyl cellulose, hydroxyethyl cellulose, alginic acid, glycerin, and salts thereof.

10. The method as set forth in claim 1, wherein the concentration of the sericin is 0.01% to 40% by weight in the denture stabilizer.

11. The method as set forth in claim 9, wherein the concentration of the thickening natural polysaccharide is 0.01% to 40% by weight in the denture stabilizer.

12. The method as set forth in claim 1, wherein the denture stabilizer is in gel or sheet form.

13. The method of claim 1, comprising the steps of incorporating the sericin into a pre-treating solution and then using the thus-prepared pre-treating solution to treat the denture surface prior to loading the denture into the oral cavity.

14. The method of claim 1, wherein the denture surface treating agent contains a combination of sericin, grapefruit extract and glycerin.

15. The method of claim 9, wherein the thickening natural polysaccharide is xanthan gum, and the denture stabilizer further contains at least one of potassium chloride, sodium chloride, dipotassium hydrogen phosphate, calcium chloride and magnesium chloride.

16. The method of claim 9, wherein the thickening natural polysaccharide is glucomannan and glycerin, and the denture stabilizer further contains grapefruit extract and at least one of potassium chloride, sodium chloride, dipotassium hydrogen phosphate, calcium chloride dihydrate and magnesium chloride hexahydrate.

* * * * *